United States Patent [19]

Rattray

[11] 4,420,709

[45] Dec. 13, 1983

[54] FLUORESCENT LAMP EMPLOYING MEANS FOR CONTROLLING EMISSION OF SHORT WAVELENGTH ULTRAVIOLET RADIATION

[75] Inventor: Kendrick D. Rattray, Danvers, Mass.

[73] Assignee: GTE Products Corporation, Stamford, Conn.

[21] Appl. No.: 319,339

[22] Filed: Nov. 9, 1981

[51] Int. Cl.³ .............................................. H01J 1/62
[52] U.S. Cl. .................................... 313/486; 313/487
[58] Field of Search ....................... 313/485, 486, 487; 128/395

[56] References Cited

U.S. PATENT DOCUMENTS 3,987,331 10/1976 Schreurs .............................. 313/486
4,251,750 2/1981 Gallien et al. ...................... 313/487

*Primary Examiner*—Palmer C. Demeo
*Assistant Examiner*—Sandra L. O'Shea
*Attorney, Agent, or Firm*—William H. McNeill

[57] ABSTRACT

Fluorescent lamp for bio-medical treatment of skin disorders includes a layer 28 of phosphor within the lamp which phosphor absorbs short wavelength U.V. radiation and re-emits the absorbed energy at a longer wavelength.

2 Claims, 3 Drawing Figures

FLUORESCENT LAMP EMPLOYING MEANS FOR CONTROLLING EMISSION OF SHORT WAVELENGTH ULTRAVIOLET RADIATION

TECHNICAL FIELD

This invention relates to the control of short wavelength ultraviolet radiation. More particularly, it relates to controlling the emission of such radiation from low-pressure mercury arc discharge lamps.

BACKGROUND ART

Low-pressure mercury arc discharge lamps, particularly of the fluorescent type having an emission spectrum primarily in the ultraviolet (U.V.) region, have been employed in the biomedical treatment of skin disorders. However, since these lamps emit a relatively broad spectrum of ultraviolet radiation, including both long wavelength U.V. (about 340 nm) and short wavelength U.V. (below 340 nm); and since in some biomedical applications the use of short wavelength U.V. is contra-indicated, the application of these lamps has been restricted. The short wavelength U.V. emissions are due, primarily, to the low-pressure mercury arc discharge itself, which has an emission peak at 313 nm, and secondarily, from the shorter wavelength emissions emanating from a phosphor coating which can be disposed within the lamp.

Prior art suggestions attempting to solve these problems have involved internal and external U.V. filtering systems, examples of which are disclosed in U.S. Pat. Nos. 3,541,376; 3,720,826; and 4,048,537. Such filtering systems tend to be expensive and, furthermore, they are non-selective in the U.V. range of 300 nm to 400 nm, ranging from high transmission at all U.V. wavelengths to very low transmission at all U.V. wavelengths.

DISCLOSURE OF THE INVENTION

It is, therefore, an object of this invention to obviate the disadvantages of the prior art.

It is another object of the invention to selectively enhance U.V. transmission.

Yet another object of the invention is the provision of a U.V. source which substantially absorbs undesirable short wavelength U.V. radiation and re-emits this absorbed energy as desirable, longer wavelength U.V. radiation.

These objects are accomplished, in one aspect of the invention, by the provision, within a lamp which includes means for generating a relatively broad spectrum of U.V. radiation, of a phosphor layer which will absorb short wavelength radiation and re-emit this absorbed energy as long wavelength U.V. radiation.

Thus, there is provided a simple and inexpensive solution to the problems enumerated above. The concept employed by this embodiment not only subtracts the detrimental short wavelength emissions from the lamp spectral power distribution, but re-emits this energy in a biochemically useful band spread.

BEST MODE FOR CARRYING OUT THE INVENTION

For a better understanding of the present invention, together with other and further objects, advantages and capabilities thereof, reference is made to the following disclosure and appended claims taken in conjunction with the above-described drawings.

Figure 1:
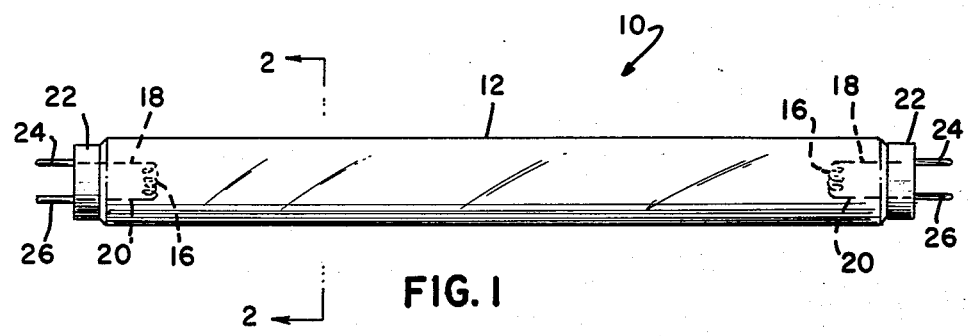
FIG. 1 is an elevational view of a lamp.

Referring now to the drawings with greater particularity, there is shown in FIG. 1 a lamp 10 comprised of a sealed hollow glass tube 12 which contains a quantity of mercury and a filling gas, such as argon. At each end of the glass tube 12 there is an electrode comprising an oxide-coated tungsten coil 16 and lead-in wires 18 and 20. Suitable bases 22 are sealed to the ends of glass tube 12 and carry contacts 24 and 26.

The lamp 10 described above is typical of the type known generally as fluorescent lamps when such lamps include on the inside surface of glass tube 12 a phosphor which will absorb the U.V. radiation generated by the mercury arc within the lamp and re-emit this energy at a different, more useful frequency. Even lamps designed to emit U.V. radiation can employ a phosphor to increase the amount of radiation emitted at a desirable frequency. Such phosphors usually respond most efficiently to U.V. energy at a wavelength of 253.7 nm since this is the wavelength generated in a mercury discharge at highest efficiency when the mercury vapor is at a pressure of about 0.008 mm. These U.V. emitting phosphors usually produce peak wavelengths between 340 nm and 380 nm; however, other, often less desirable wavelengths also are produced. The mercury arc, itself, produces also other frequencies of U.V., in particular a peak at 313 nm.

Figures 2, 3:
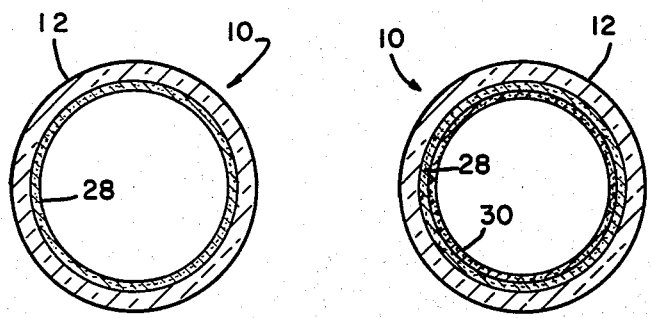
FIG. 2 is a sectional view taken along the line 2—2 of FIG. 1.
FIG. 3 is a sectional view, similar to FIG. 2, illustrating another embodiment.

In the cross-section of lamp 10 shown in FIG. 2, a first phosphor 28 is provided within glass tube 12, on the interior wall thereof. Phosphor 28 is preferably a strontium fluoroborate activated by europium and generally depicted as $SrB_4O_7(F):Eu$. This material absorbs, or is energized by, U.V. radiation having a wavelength of 313 nm and re-emits this absorbed energy at about 370 nm.

In FIG. 3, lamp 10 is shown as including a second phosphor 30 overlying phosphor 28. Phosphor 30 can be any suitable U.V. emitting material having its primary wavelengths greater than 340 nm.

Such a phosphor, for example, can be a cerium barium magnesium aluminate.

The reduction in the undesirable short wavelength U.V. radiation accomplished by this invention is shown by the table below wherein phosphor 28 is strontium fluoroborate: europium and phosphor 30 is cerium barium magnesium aluminate. Both of these phosphors are available from GTE Sylvania, Towanda, Pa.

| Coating Wgt. Phosphor 28 | Coating Wgt. Phosphor 30 | U.V. Emitted <340 nm | U.V. Emitted 340–400 nm |
|---|---|---|---|
| None (control) | 4.79 gms | 2.62 watts | 7.71 watts |
| 0.08 gms | 4.79 gms | 2.08 watts | 7.48 watts |
| 0.19 gms | 4.79 gms | 1.79 watts | 6.97 watts |

It can be seen from the table that employment of this invention provides a significant reduction in the undesired U.V. below 340 nm with only a minor reduction in the desired higher frequencies.

While there have been shown and described what are at present considered to be the preferred embodiments of the invention, it will be apparent to those skilled in the art that various changes and modifications can be made herein without departing from the scope of the invention as defined by the appended claims.

I claim:

1. A fluorescent lamp useful in the biomedical treatment of skin disorders, said lamp comprising means for generating a relatively broad spectrum of ultra violet radiation including desirable long wavelength radiation and less desirable short wavelength radiation, the improvement comprising: a layer of a first phosphor within said lamp, said first phosphor being adhered to the interior surface of said lamp and absorbing said short wavelength radiation and re-emitting this absorbed energy as said long wavelength radiation; said means for generating said relatively broad spectrum of ultraviolet radiation including a low pressure mercury arc discharge and a second layer of phosphor overlying said first phosphor.

2. The lamp of claim 1 wherein said first phosphor is an europium activated strontium fluoroborate.

* * * * *